(12) United States Patent
Shinozaki et al.

(10) Patent No.: US 8,691,003 B2
(45) Date of Patent: Apr. 8, 2014

(54) COMPOSITION FOR INDICATOR WITH WHICH USED FOR DETECTING PRESSURE POINTS ON DENTURE

(75) Inventors: Yutaka Shinozaki, Itabashi-ku (JP); Hiroshi Kamohara, Itabashi-ku (JP)

(73) Assignee: GC Corporation, Tokyo (JP)

( * ) Notice: Subject to any disclaimer, the term of this patent is extended or adjusted under 35 U.S.C. 154(b) by 210 days.

(21) Appl. No.: 13/248,557

(22) Filed: Sep. 29, 2011

(65) Prior Publication Data

US 2012/0079961 A1 Apr. 5, 2012

(30) Foreign Application Priority Data

Sep. 30, 2010 (JP) ................................. 2010-221418

(51) Int. Cl.
*A61K 6/00* (2006.01)

(52) U.S. Cl.
USPC ............... 106/35; 523/109; 433/71; 524/197; 524/21; 524/27; 524/28; 524/36; 524/42; 524/43; 524/45; 524/47; 524/49; 524/51; 106/148.1; 106/156.21; 106/156.22; 106/157.1; 106/166.51; 106/169.51; 106/179.1; 106/182.1; 106/184.1; 106/184.3; 106/196.1; 106/205.1; 106/205.5; 106/205.7; 106/205.8; 106/215.3; 106/215.4; 106/216.1; 106/272

(58) Field of Classification Search
USPC ..................... 523/109; 433/71; 106/35, 148.1, 106/156.21, 156.22, 157.1, 166.51, 169.51, 106/179.1, 182.1, 184.1, 1, 84.3, 196.1, 106/205.1, 205.5, 205.17, 205.8, 215.3, 106/215.4, 216.1, 272; 524/19, 21, 27, 28, 524/36, 42, 43, 45, 47, 49, 51
See application file for complete search history.

(56) References Cited

U.S. PATENT DOCUMENTS

| 3,028,247 | A | 4/1962 | Molnar |
| 3,966,925 | A | 6/1976 | Bell |
| 4,198,243 | A | 4/1980 | Tanaka |
| 5,116,222 | A | 5/1992 | Futami et al. |
| 2008/0057465 | A1 * | 3/2008 | Kamohara et al. ............ 433/48 |

FOREIGN PATENT DOCUMENTS

| EP | 0 003 638 A2 | 8/1979 |
| EP | 0 003 638 A3 | 8/1979 |
| GB | 2 226 039 A | 6/1990 |
| GB | 2226039 | * 6/1990 |
| JP | 51-61611 | 5/1976 |
| JP | 2-262502 | 10/1990 |
| JP | 2-264705 | 10/1990 |

OTHER PUBLICATIONS

Extended European Search Report issued Nov. 29, 2011, in Patent Application No. 11007965.4.

* cited by examiner

*Primary Examiner* — Carol M Koslow
(74) *Attorney, Agent, or Firm* — Oblon, Spivak, McClelland, Maier & Neustadt, L.L.P.

(57) ABSTRACT

An indicator is useful for detecting pressure points on a denture. The indicator is made of a composition that easily adheres to oral mucosa, has a proper viscosity in an oral cavity environment, can be properly spread between an oral mucosa surface and a denture base, and easily specifies an affected part. The composition includes a fatty acid ester having a melting point of 30 to 50° C., a water-soluble high polymer, and a metal oxide. Preferably, the fatty acid is 40 to 95% by weight of the composition, the water-soluble high polymer is 1 to 59% by weight of the composition, and the metal oxide is 0.1 to 50% by weight of the composition.

5 Claims, No Drawings

COMPOSITION FOR INDICATOR WITH WHICH USED FOR DETECTING PRESSURE POINTS ON DENTURE

BACKGROUND OF THE INVENTION

1. Field of the Invention

The present invention relates to a composition for an indicator with which used for detecting pressure points on denture capable of accurately imprinting, on a denture base mucosa surface, a position of an ulcer developed in an oral mucosa, a position of a bone sharp tip part, or the like.

2. Description of the Conventional Art

When a plurality of teeth is lost due to aging or an accident, prosthesis with a partial denture or a full denture has been generally performed. A denture is configured by arraying artificial teeth on a denture base, and the entire denture can be stabilized directly contacting the denture base to the oral mucosa. Therefore, compatibility of the denture base to the oral mucosa is extremely important.

When producing the denture, the denture is sufficiently adjusted so as to fit with the oral mucosa. However, when the denture is actually mounted, the denture base may not fit with oral mucosa due to dimensional change of a material or error in the production process (i.e., an unfitting portion may be formed). As for a method for adjusting the unfitting portion, a fit checking material, such as a white-based ointment-like coating material, a white-based room temperature-polymerizable silicone, or the like, is coated on the oral mucosa surface side. After the denture is mounted in the oral of a patient and imprinted by an oral mucosa surface shape, the denture is taken out from the oral and observed. A portion at which the fit checking material is pushed away, i.e., a strongly contacting overpressure portion, is checked. Then, the overpressure part of the denture base is grinded, and a lining material for a denture base is added to a portion with a gap between the oral mucosa surface and the denture base, at which the fit checking material remains. By repeating this operation, the overpressure portion disappears, and the entire denture base is in uniformly contact with the oral mucosa.

Even if a denture is compatible, when the denture base is mounted for a long period of time, redness or an ulcer is generated in an oral mucosa portion which is locally over-pressurized due to absorbing, deforming or the like of a jawbone. In this case, it is specified which part of denture base over-pressurizes the oral mucosa, and the specified portion of the denture base is adjusted by grinding or the like. However, since the portion generating the redness or ulcer is local, it is difficult to accurately grasp the specified portion of the denture base only with the fit checking material. In this case, using an instrument, a dentist applies a small amount of a composition colored to be easily distinguished from the oral tissue to the portion of a patient at which the redness or ulcer is generated (regarding the composition, e.g. refer to Japanese Patent Application Laid-Open No. S51-061611, Japanese Patent Application Laid-Open No. H2-262502, and Japanese Patent Application Laid-Open No. H2-264705). Then, the dentist mounts the denture to the patient, imprints the portion of the patient on the denture base, grasps the specified portion of the denture base, and then performs an adjustment operation by grinding the specified portion.

As described above, a composition applied for locally diagnosing an overpressure part needs a property to fully adhere and remain when it is coated to an affected part in the oral mucosa, and needs a property to easily adhere to the oral mucosa surface side of the denture base. A conventional fit checking material uses, as a base material, a low hydrophilic base material such as liquid paraffin, polydiorganosiloxane, or the like. Therefore, the fit checking material blends with a dry powdery adhesive or a water-soluble polymer in order to easily adhere to the oral mucosa, so that the composition temporarily adheres to the oral mucosa. However, the composition still often adheres to only the denture side, so that it cannot accurately confirm whether the position of the affected part generating the redness or ulcer is imprinted on the denture. Further, in order to easily adhere to the affected part, the composition uses multifunctional alcohol such as glycerin, or the like, as a base material, or blends with a dry powdery adhesive or a water-soluble high polymer at a high concentration. However, the composition comes to be easily dissolved with moisture in this case, so that the composition is spread too much between the denture base and the oral mucosa. Thus, it is difficult to accurately specify the portion which is locally over-pressurized to generate the redness or ulcer.

SUMMARY OF THE INVENTION

An objective of the present invention is to provide a composition for a indicator with which used for detecting pressure points on denture, which easily adheres to an oral mucosa and remains, has proper viscosity in an oral, has a property to be properly spread between an oral mucosa surface and a denture base, and easily specifies an affected part.

Present inventors carried out earnest works to solve the aforementioned problems and, as a result, they found out the following composition for a indicator with which used for detecting pressure points on denture to complete the present invention. The composition uses fatty acid ester having a melting point within a specific temperature range, a water-soluble high polymer, and a metal oxide. Accordingly, the composition has adhesion in relation to an oral mucosa and proper consistency.

Namely, the present invention is a composition for a indicator with which used for detecting pressure points on denture, which includes a fatty acid ester having a melting point of 30 to 50° C., a water-soluble high polymer and a metal oxide.

The composition according to the present invention is a composition for a indicator with which used for detecting pressure points on denture, which easily adheres to an oral mucosa and remains, has proper viscosity in an oral, has a property to be properly spread between an oral mucosa surface and a denture base, and easily specifies an affected part.

DETAILED DESCRIPTION OF PREFERRED EMBODIMENTS

Fatty acid ester (A) having a melting point of 30 to 50° C. and being used for a composition for diagnosing an overpressure part according to the present invention is an ester compound which includes fatty acid and alcohol and has a melting point of 30 to 50° C. If the melting point is less than 30° C., the fatty acid ester comes to be liquid easily at around a room temperature, so that operability comes to be low when coating the composition by using an instrument or the like. If the melting point exceeds 50° C., the fatty acid ester is hardly melted at a body temperature, so that it cannot be used. The fatty acid ester having a melting point of 30 to 50° C. has excellent operability when coating a small amount of the composition to a portion at which the redness or ulcer is generated around the room temperature by using an instrument or the like. After coating the composition, the fatty acid ester has proper viscosity at a body temperature, and easily flows when pressure is applied. Further, the fatty acid ester having a melting point of 30 to 50° C. has, by itself, a property holding and containing moisture within a range from about a body temperature to a slightly higher temperature than the body temperature (this property is called hydatability in general), so that the fatty acid ester is easy to be compatible with moisture. Thus, the fatty acid ester can easily adhere to an oral mucosa. In addition, the fatty acid ester does not flow out in an oral containing much moisture, so that proper viscosity and flowability can be secured. Furthermore, a low hydrophilic material such as polydiorganosiloxane or the like is not used in the present invention because it prevents adhesion to the oral mucosa.

More specifically, as the fatty acid ester (A) having a melting point of 30 to 50° C., ethyl stearate, cetyl myristate, cholesteryl isostearate, octadecyl laurate, tetradecyl myristate, decyl palmitate, dodecyl palmitate, tetradecyl palmitate, propyl stearate, amyl stearate, octyl stearate, sebacic acid monomethyl ester, sebacic acid monoethyl ester, or the like can be used. Lanolin or whale wax which includes ester of higher alcohol and higher fatty acid as a main component, beef tallow, lard, horse fat, mutton tallow, cocoa butter, palm oil, trilaurin, trimyristin, 1-caprylyl-2,3-distearin, 1-myristoyl-2,3-dicaprin, 1-palmitoyl-2,3-dicaprin, 1-stearoyl-2,3-dicaprin, 2-lauroyl-1,3-dicaprin, 1-caproyl-2,3-dilaurin, 2-myristoyl-1,3-dicaprin, 1-caproyl-2,3-dimyristin, 2-palmitoyl-1,3-dicaprin, 1-caproyl-2,3-dipalmitin, 2-stearoyl-1,3-dicaprin, 2-caproyl-1,3-dilaurin, 1-myristoyl-2,3-dilaurin, 2-palmitoyl-2,3-dilaurin, 1-caproyl-2,3-distearin, 1-stearoyl-2,3-dilaurin, 2-myristoyl-1,3-dilaurin, 1-lauroyl-2,3-dimyristin, 2-palmitoyl-1,3-dilaurin, 1-lauroyl-2,3-dipalmitin, 2-stearoyl-1,3-dilaurin, 1-lauroyl-2,3-dielaidin, 2-caproyl-1,3-dimyristin, 2-lauroyl-1,3-dimyristin, 1-elaidyl-2,3-dimyristin, 1-myristoyl-2,3-dielaidin, 2-lauroyl-1,3-dipalmitin, 1-oleoyl-2,3-dipalmitin, 2-oleoyl-1,3-dipalmitin, 1-oleoyl-2,3-distearin, 1-linoleoyl-2,3-distearin, 2-oleoyl-1,3-distearin, 1-stearoyl-2-myristoyl-3-caprin, 1-stearoyl-2-lauroyl-3-caprin, 1-stearoyl-2,3-dicaprin, 1,3-dicaprin, diundecanoin or the like, which mainly includes triester of fatty acid and glycerine as a main component, can be preferably used. In particular, since lanolin is having a melting point of 37 to 43° C. which is slightly higher than around the body temperature, it has sufficient operability, adhesion to an affected part, and proper viscosity, so that lanolin is preferable.

It is preferable that 40 to 95% by weight of the fatty acid ester (A) having a melting point of 30 to 50° C. is blended in the composition. More preferably, 60 to 90% by weight of the fatty acid ester (A) is blended. If the blending ratio is less than 40% by weight, the composition is easily spread, so that it is not preferable. If the blending ratio exceeds 95% by weight, it results in decreasing of the blending ratios of other components. If the blending ratio of a water-soluble high polymer decreases, the composition comes to be hard to adhere to the oral mucosa. If the blending ratio of a metal oxide decreases, it is hard to distinguish the composition from the oral mucosa or a denture base.

A water-soluble high polymer (B) has a function to be combined with the fatty acid ester (A) to make a paste composition. In addition, the water-soluble high polymer (B) absorbs moisture in the oral to increase viscosity of the composition. Furthermore, the water-soluble high polymer (B) works to improve adhesion to the oral mucosa. The water-soluble high polymer (B) used in the present invention is, for example, sodium alginate, potassium alginate, carboxymethylcellulose, polyvinylpyrrolidone, polyacrylic acid, polyvinyl alcohol, soluble starch, carboxyl starch, British rubber, dialdehyde starch, dextrin, cation starch, viscose, methylcellulose, ethylcellulose, hydroxyethylcellulose, polyethylene glycol, polypropylene glycol, polyacrylamide, water-soluble alkyd, polyvinyl ether, a polymaleic acid copolymer, polyethyleneimine, sodium polyphosphate, water glass, agar, starch, plant mucilage, animal protein, or the like. Among these materials, sodium alginate and potassium alginate are preferable in lights of swelling property, gelling property and viscosity in the oral.

It is preferable that 1 to 59% by weight of the water-soluble high polymer (B) is blended in the composition. More preferably, 10 to 40% by weight of the water-soluble high polymer (B) is blended. If the blending ratio is less than 1% by weight, effect to improve the viscosity of the composition cannot be obtained, and the adhesion to the oral mucosa decreases, so that it is not preferable. If the blending ratio exceeds 59% by weight, the viscosity of the composition in the oral comes to be too high, and an outer periphery of the paste adhering to the oral mucosa is un-uniformly spread as with dissolving in moisture, so that it comes to be difficult to accurately grasp the position of a specified part. So, it is not preferable.

A metal oxide (C) is blended to color the composition, so that the composition adhering to the oral mucosa or the denture base can be easily distinguished from the oral mucosa or the denture base. Thus, the metal oxide is used for accurately grasping the specified part. More specifically, powders of titanium oxide, zinc oxide, zirconium oxide, aluminum oxide, magnesium oxide, iron oxide, powders of composite metal oxide, or the like can be used.

It is preferable that 0.1 to 50% by weight of the metal oxide (C) is blended in the composition. More preferably, 1 to 30% by weight of the metal oxide (C) is blended. If the blending ratio is less than 0.1% by weight, the composition is not fully colored, so that it is hard to distinguish the composition from the oral mucosa or the denture base. If the blending ratio exceeds 50% by weight, operability comes to be extremely deteriorated, so that it is not proper.

In addition, in the composition for the indicator with which used for detecting pressure points on denture according to the present invention, as necessary, various kinds of an antibacterial material, an inorganic filler, a perfume, an antioxidant, an anti-discoloring agent, a colorant other than metal oxides, or the like can be added within a range not damaging the properties as necessary.

The present invention will be described in detail below with reference to examples. However, the present invention is not limited to these examples.

The composition for the indicator with which used for detecting pressure points on denture, which is produced at a blending ratio shown in Table 1, was coated to an ulcer part of a patient by using an instrument. Then, after a denture was mounted to the patient and occluded for one minute, the denture was removed from an oral and visually observed. The adhesion to an oral mucosa when coating the composition, a spreading state of the composition when removing the denture, and an easiness of confirmation were evaluated as follows. These results were shown in Table 1 collectively.

<Evaluation Standard of Easiness of Adhesion to an Oral Mucosa>

A: The composition easily adheres to an oral mucosa when coating the composition and remains on the oral mucosa, and also the denture is imprinted when removing the denture.

B: Although the composition easily adheres to an oral mucosa when coating the composition, the composition does not remain on the oral mucosa and wholly adheres to the denture.

C: The composition hardly adheres to an oral mucosa when coating the composition, does not remain on the oral mucosa when removing the denture, and wholly adheres to the denture.

<Evaluation Standard of a Spreading State of the Composition>

A: A spreading state of the composition is proper, and an accurate position of the affected part can be grasped.

B: Although a spreading state of the composition is a little large, a position of the affected part can be mostly confirmed.

C: A spreading state of the composition is too large, and a position of the affected part is hardly grasped.

TABLE 1

| | | Example 1 | Example 2 | Example 3 | Example 4 | Comparative example 1 | [% by weight] Comparative example 2 |
|---|---|---|---|---|---|---|---|
| Fatty acid ester | Lanolin | 88 | 60 | 65 | | | |
| | Lard | | | | 75 | | |
| With fatty acid ester | Liquid paraffin | | | | | 60 | |
| | Glycerin | | | | | | 45 |
| Water-soluble high polymer | Sodium alginate | 10 | | | 10 | 39 | |
| | Potassium alginate | | 30 | | | | 41 |
| | Carboxymethylcellulose | | | 15 | | | |
| | Polyvinylpyrrolidone | | | | 10 | | |
| Metal oxide | Titanium oxide | 2 | | 10 | 5 | 1 | |
| | Zinc oxide | | 10 | | | | 14 |
| | Iron oxide | | | 10 | | | |
| Adhesion to an oral cavity mucosa | | A | A | A | A | C | B |
| Spreading state | | A | A | A | A | B | C |

Clearly from Table 1, it was confirmed that Examples 1 to 4 had adhesion to the oral mucosa, had a proper spreading state of the composition, and could be easily confirmed. On the other hand, Comparative examples 1 and 2 had insufficient adhesion to the oral mucosa, had a low spreading state of the composition, and could be hardly confirmed.

What is claimed is:

1. A composition, comprising:
   from 40 to 95% by weight of a fatty acid ester having a melting point of from 30 to 50° C.;
   from 1 to 59% by weight of a water-soluble high polymer; and
   from 0.1 to 50% by weight of a metal oxide,
   wherein the composition is suitable for detecting a pressure point on a denture.

2. A method for detecting a pressure point on a denture, the method comprising detecting a pressure point on a denture with the composition of claim 1.

3. The method of claim 2, further comprising applying the composition to oral mucosa.

4. The method of claim 2, further comprising applying the composition to an ulcer part of a patient.

5. The method of claim 4, further comprising:
   mounting a denture to the patient after the applying, and then
   removing the denture.

* * * * *